(12) United States Patent
Hill et al.

(10) Patent No.: US 8,625,866 B2
(45) Date of Patent: Jan. 7, 2014

(54) IMAGE DATA MANAGEMENT SYSTEMS

(75) Inventors: Derek Lionel Glendon Hill, London (GB); Kate McLeish, London (GB); Joseph Vilmos Hajnal, London (GB); Shahid Jamil, London (GB); Mark Robert Austin, Kent (GB)

(73) Assignee: Ixico Limited, London (GB)

( * ) Notice: Subject to any disclaimer, the term of this patent is extended or adjusted under 35 U.S.C. 154(b) by 64 days.

(21) Appl. No.: 13/055,838

(22) PCT Filed: Jul. 24, 2009

(86) PCT No.: PCT/GB2009/050919
§ 371 (c)(1),
(2), (4) Date: Apr. 11, 2011

(87) PCT Pub. No.: WO2010/010403
PCT Pub. Date: Jan. 28, 2010

(65) Prior Publication Data
US 2011/0188718 A1 Aug. 4, 2011

(30) Foreign Application Priority Data

Jul. 25, 2008 (GB) .................................. 0813666.5

(51) Int. Cl.
*G06K 9/00* (2006.01)
(52) U.S. Cl.
USPC ......................................... 382/128; 382/131
(58) Field of Classification Search
USPC ......... 382/100, 128–134, 173, 181, 190, 276, 382/294, 305, 307; 378/38, 62, 168, 192; 370/392, 26; 128/922; 600/300, 410, 600/420, 407, 509; 601/162; 701/1; 702/19; 705/2–4; 707/687, 690, 705, 769–771, 707/802; 709/247; 715/234, 733; 726/26
See application file for complete search history.

(56) References Cited

U.S. PATENT DOCUMENTS

| | | | |
|---|---|---|---|
| 6,269,177 B1 * | 7/2001 | Dewaele et al. ............... | 382/131 |
| 6,330,685 B1 | 12/2001 | Hao et al. | |
| 7,158,692 B2 * | 1/2007 | Chalana et al. ................ | 382/294 |
| 7,860,287 B2 * | 12/2010 | Zahlmann et al. ............. | 382/128 |
| 7,979,522 B2 * | 7/2011 | Lunsford ....................... | 709/223 |
| 2004/0064037 A1 * | 4/2004 | Smith ............................. | 600/420 |
| 2005/0031181 A1 * | 2/2005 | Bi et al. .......................... | 382/132 |
| 2005/0063575 A1 * | 3/2005 | Ma et al. ........................ | 382/128 |
| 2006/0155585 A1 | 7/2006 | Onishi | |
| 2006/0251305 A1 * | 11/2006 | Mohr ............................. | 382/128 |

(Continued)

FOREIGN PATENT DOCUMENTS

| | | |
|---|---|---|
| EP | 1657681 A1 | 5/2006 |
| JP | 2004290259 A | 10/2004 |
| WO | 2007116899 A1 | 10/2007 |
| WO | 2008038614 A1 | 4/2008 |

*Primary Examiner* — Hadi Akhavannik
*Assistant Examiner* — Mehdi Rashidian
(74) *Attorney, Agent, or Firm* — Fraser Clemens Martin & Miller LLC; William J. Clemens

(57) ABSTRACT

A system for admitting medical imaging data comprising image data and associated metadata comprises input means arranged to received image data from at least one source, a memory having stored therein consistency data defining at least one consistency criterion, and processing means arranged to analyze the imaging data to determined whether it meets the consistency criterion, and if it does not to amend the imaging data so that it does.

15 Claims, 4 Drawing Sheets

(56) References Cited

U.S. PATENT DOCUMENTS

| | | | |
|---|---|---|---|
| 2008/0031505 A1* | 2/2008 | Barski et al. | 382/132 |
| 2008/0058611 A1* | 3/2008 | Tsubura | 600/300 |
| 2008/0085042 A1* | 4/2008 | Trofimov et al. | 382/128 |
| 2009/0299771 A1* | 12/2009 | Hsieh et al. | 705/3 |
| 2010/0098309 A1* | 4/2010 | Graessner et al. | 382/131 |
| 2010/0274116 A1* | 10/2010 | Blum et al. | 600/407 |
| 2011/0110572 A1* | 5/2011 | Guehring et al. | 382/131 |
| 2011/0176712 A1* | 7/2011 | Hill et al. | 382/128 |

* cited by examiner

| Subject ID | Visit 1 | Visit 2 | Visit 3 | Visit 4 | Visit 5 |
|---|---|---|---|---|---|
| S0010001 | lm1, lm2, lm3 | lm1, lm2, lm3 | lm1, lm2, lm3 | lm1, lm2, lm3 | lm1, lm2, lm3 |
| S0010002 | lm1, lm2, lm3 | lm1, lm2, lm3 | lm1, lm2, lm3 | lm1, lm2, lm3 | lm1, lm2, lm3 |
| S0020001 | lm1, lm2, lm3 | lm1, lm2, lm3 | lm1, lm2, lm3 | lm1, lm2, lm3 | lm1, lm2, lm3 |
| S0020002 | lm1, lm2, lm3 | lm1, lm2, lm3 | lm1, lm2, lm3 | lm1, lm2, lm3 | lm1, lm2, lm3 |
| S0030001 | lm1, lm2, lm3 | lm1, lm2, lm3 | lm1, lm2, lm3 | lm1, lm2, lm3 | lm1, lm2, lm3 |
| S0030002 | lm1, lm2, lm3 | lm1, lm2, lm3 | lm1, lm2, lm3 | lm1, lm2, lm3 | lm1, lm2, lm3 |
| S0030003 | lm1, lm2, lm3 | lm1, lm2, lm3 | lm1, lm2, lm3 | lm1, lm2, lm3 | lm1, lm2, lm3 |
| S0030004 | lm1, lm2, lm3 | lm1, lm2, lm3 | lm1, lm2, lm3 | lm1, lm2, lm3 | lm1, lm2, lm3 |
| S0040001 | lm1, lm2, lm3 | lm1, lm2, lm3 | lm1, lm2, lm3 | lm1, lm2, lm3 | lm1, lm2, lm3 |

*Fig. 5*

IMAGE DATA MANAGEMENT SYSTEMS

FIELD OF THE INVENTION

The present invention relates to data management systems and in particular to systems for managing data, such as image data (radiological, histological etc.), collected and/or analyzed as part of clinical trials or in healthcare.

BACKGROUND TO THE INVENTION

In clinical trials that involve imaging, there is a need to upload data into a validated computer system for storage and/or analysis, and in doing so, to ensure that the data is compliant with any data privacy legislation, that it is "clean" (i.e. correctly labelled and error free), and that any problem data is flagged, and that relevant parties are notified. All handling of the images must be compliant with relevant regulations (e.g. ICH-GCP and 21 cfr pt 11).

Clinical image data is frequently transferred as DICOM format, either across a network or on removable media. The DICOM image format includes the image, and also a header containing metadata that relates to the subject and the acquired images. For clinical trial use, it is accompanied by a paper or electronic form that contains associated information which is not included in the DICOM metadata (e.g. the trial identifier, time-point in the trial, any comments made by the collecting site), and may also be accompanied by other data files. While DICOM provides a standard format for image transfer and storage, it does not standardize many of the components of the DICOM header (which includes a number of tags), which are entered by the person operating the scanner. Such tags include the Series Description, which defines the type of scan (e.g. T1 weighted vs T2 weighted MRI scan) and will invariably depend on the language spoken in the country where the data is collected, procedures at that site, and is additionally prone to human error. Furthermore, the DICOM tags do not contain certain relevant information required in clinical trials, such as a precise description of the anatomy imaged (so that checks can be made that the correct anatomy was imaged), the compound being used or its mode of action, and many types of data required for the quantitative analysis of image data. Also, while DICOM is widely used, it is not a universally supported format—especially for analysed results—and so other formats need to be handled also, and these have different ways of storing metadata, sometimes primarily in the file name and folder names that contain these files.

Current methods for importing clinical trial data require substantial user interaction, manual resolution or correction of ambiguities in the metadata (which we refer to as correction of mis-labelling errors), and visual identification of problem data. Systems are available that check the DICOM metadata for conformance, but the DICOM data alone does not provide all the relevant information (e.g. visit number), and other associated files that are needed to complete the analysis, or that result from the analysis, are often not in DICOM format. In many cases mis-labellings or incomplete data will go undetected resulting in erroneous results being included in the analysis, and these errors may not be detected before the results are used in decision making or are submitted to regulators for the approval of the drug.

Current methods for storing image data are also not amenable to aggregation of data from multiple trials for re-analysis or meta-analysis, and to achieve this, it is necessary to add additional metadata on import so that searches across trials can be performed, eg: on mode of action of drugs, pathology recruited etc.

With the advent of personalized healthcare, it is becoming increasingly common for patients to be imaged multiple times as part of diagnosis or treatment protocols. The same challenges arise in these circumstances as arise in clinical trials, especially since a patient's images are unlikely to all be collected on the same scanner or even at the same hospital. Also aggregation of data from numerous patients treated at multiple hospitals has benefits for clinical audit evidence based medicine.

SUMMARY OF THE INVENTION

The present invention provides a system for admitting medical imaging data comprising image data and associated metadata, the system comprising input means arranged to receive image data from at least one source, a memory having stored therein consistency data defining at least one consistency criterion, and processing means arranged to analyse the imaging data to determine whether it meets the consistency criterion, and if it does not to amend the imaging data so that it does. The associated metadata here may, for example, include one or more of the following: data inside the image files (in headers), data entered on separate forms, data in separate files (e.g.: spreadsheets, physiological monitoring out put), and results of analysis including annotated images or interim results; and for each file, MIME type, file name, folder name, computer name or address, or the ID of the user who created or transferred the file The system may be arranged to admit the data for at least one of storage and analysis.

The present invention, in some embodiments, makes use of the fact that, for all clinical trials, and for properly protocoled patient management in healthcare, the expected types of images, the part of the subject to be imaged, the type of associated data or associated files, the timing of acquisition, and the analysis results to be obtained from these images, is pre-defined by the protocol that is fixed before the data collection begins, with any revisions being properly documented. Similarly for histological studies there is, in appropriate cases, a protocol which defines the times and types of the images. This provides important prior information about what is expected. Similarly, example images of each type (with the same physical properties and of the correct anatomy) are likely to be available e.g. from a previous subjects being imaged with a similar protocol (E.g. a previous clinical trial), collected as dedicated reference data, or collected during a preparatory period (e.g: site qualification) before patients are recruited.

In a clinical trial, it is standard practice for result from all subjects to be analysed together, so data needs to be aggregated for all subjects. In healthcare applications, the data from each subject is normally considered separately in order to manage that patient. Increasingly, however, it is desirable to aggregate results from multiple subjects across different hospitals e.g. for clinical audit purposes.

The present invention provides, in some embodiments, a system that can import DICOM images with accompanying non-DICOM metadata and analysis results, automatically clean it, and correctly populate an image database or repository. Any problem data needs to be identified, any mis-labelling or ambiguous labelling resolved, and the images and associated data correctly assigned to scan type, subject, site, time point, trial etc. The data might need to be imported all in one go (e.g. at the end of a trial), or as the trial proceeds.

Where the data is imported as the trial proceeds, the identification of missing or mis-labelled data can be performed in real-time to enable any errors to be resolved automatically, or by the means of user-interaction, at the time of import.

Preferred embodiments of the present invention will now be described by way of example only with reference to the accompanying drawings.

BRIEF DESCRIPTION OF THE DRAWINGS

FIG. 5 is a table showing part of an image data set used in the system of FIG. 1.

DESCRIPTION OF THE PREFERRED EMBODIMENTS

Figure 1:
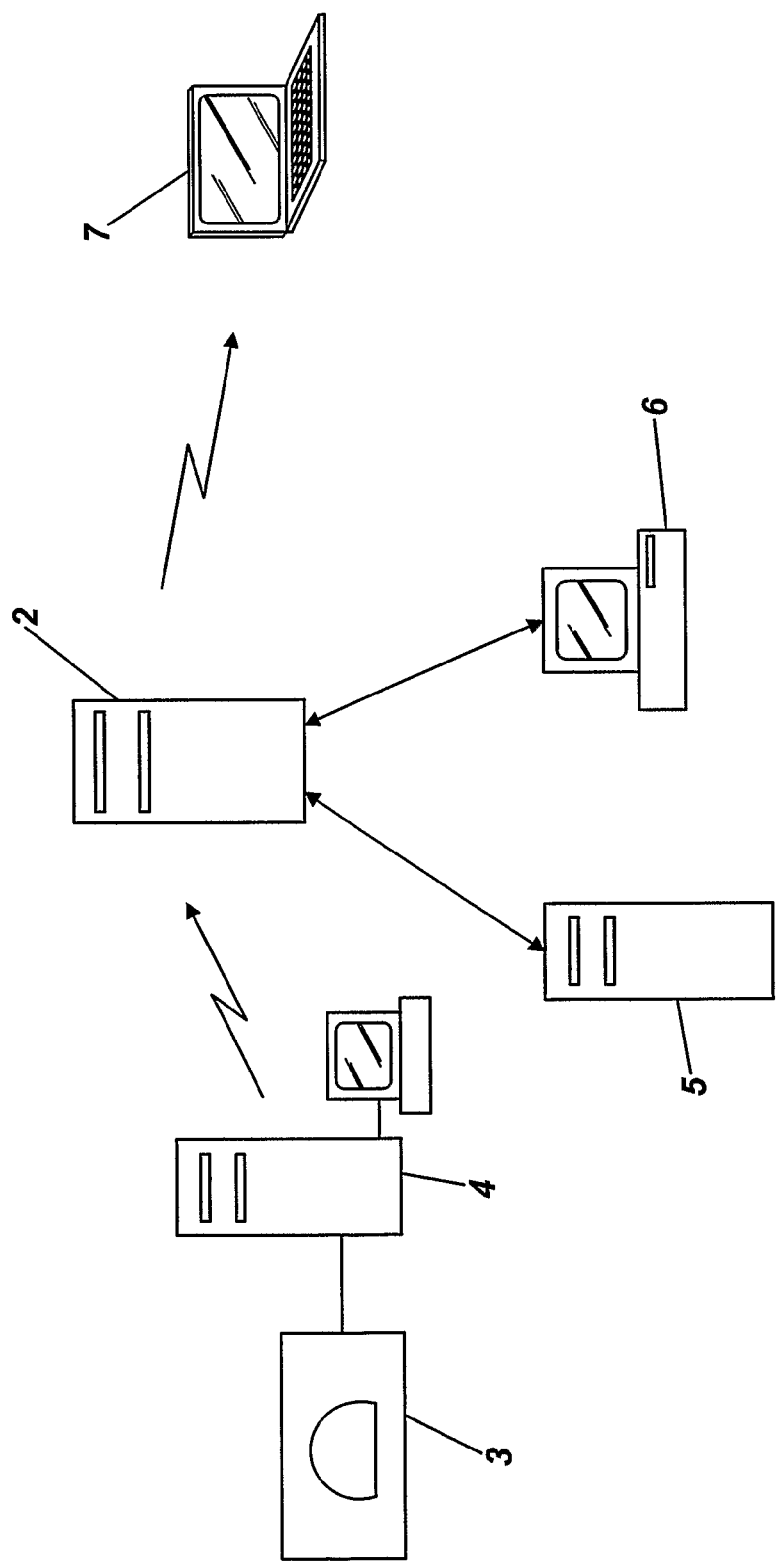
FIG. 1 is a diagrammatic representation of a data management system according to an embodiment of the invention

Referring to FIG. 1, an imaging data management system is arranged to manage data on a central server 2 at a central site. Data can be uploaded from a number of sites, for example from a number of scanners 3 (only one of which is shown) via computers 4 at each scanner site. Associated data may be loaded up both from the same computer as the images and/or from separate computers. Tasks can be scheduled to computers 5, if they can be performed automatically, and to workstations 6 if they are to be performed manually. The results of the trial can be reported to a client system 7.

Figure 2:
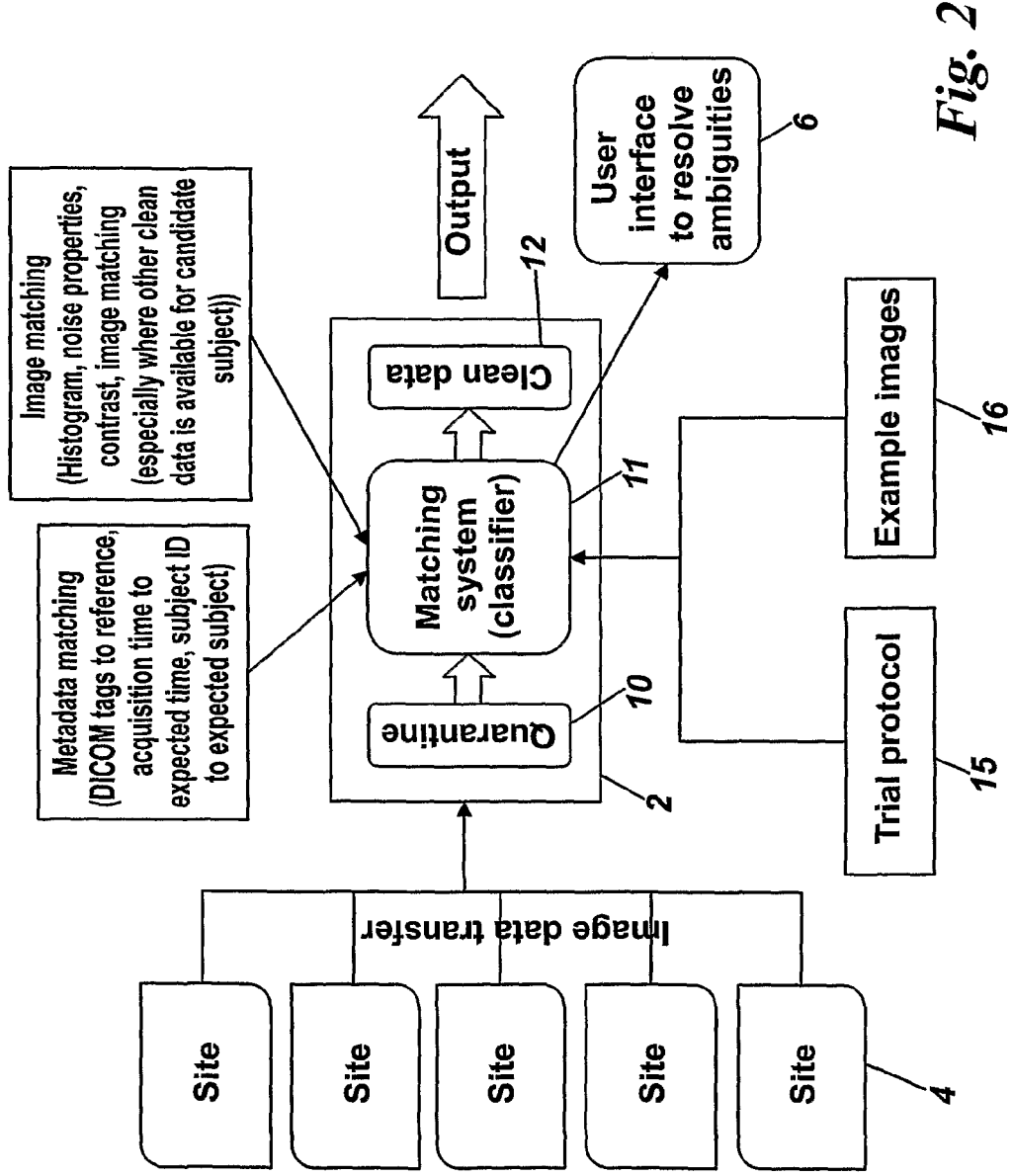
FIG. 2 is a functional representation of a data uploading part of the data management system of FIG. 1.

Referring to FIG. 2, the central server 2 is arranged to receive imaging data, in the form of actual image data, and associated metadata. This may be in the form of DICOM files, and comes from computers 4 at the scanner sites. The central server 2 is further arranged to perform a number of data checking and cleaning tasks, and to output the cleaned data for example to provide reports to the client 7. The central server 2 includes a first memory area that serves as a quarantine 10 in which incoming data is held, a matching system 11, typically comprising a processor, arranged to perform the various checking and cleaning tasks that will be described in more detail below, and a further memory area 12 for holding the cleaned data ready for exporting (e.g.: for subsequent analysis).

In clinical trials, because the image data is acquired from multiple sites, may have multiple problems including:

The images are typically not labelled consistently between sites, between scanners at a single site, or for images acquired at the same scanner at different timepoints. For example, an MR scan that is T2 weighted might be labelled as "T2w" at one site, "T2 weighted" at a second, and "FSE" at a third. Similar ambiguities will be present in labels in the headers of images from other modalities including CT, PET and ultrasound.

In clinical trials, some sites may correctly enter subject information in a de-identified format (e.g. replace subject name with an identifier, and replace date of birth with year of birth) but this may not be done consistently. Users may also accidentally mis-type the subject identifier or use an incorrect identifier. In the clinical context subject details may be incorrect or even completely inappropriate (e.g. examinations for two subjects interchanged).

Numerous different combinations of hardware and software are used in scanners, so the images will be acquired slightly differently at different sites involved in a multi-centre clinical trial, or at different hospitals providing care for patients undergoing diagnosis and treatment according to a similar protocol. For the data to be considered standardized, variations between sites should be within a defined range, and each site should apply the same acquisition protocol consistently for all subjects they scan at all time points.

Some image or associated data may be missing, because of transfer errors, because of failure of the site to follow the protocol, because the subject did not attend an appointment, or because the subject could not remain in the scanner for the full examination.

The images may not contain the correct anatomical region of interest as defined in the protocol, or may not contain the corresponding anatomical region at each time point (eg: chest, abdomen and pelvis at baseline, but only chest at repeat scanning).

There may be unexpected data e.g. scans repeated due to motion, scans obtained because an unexpected change in the disease or a possible side effect (adverse event) was being investigated, extra image data or associated data that is not required.

Data may be sent that is from the wrong trial.

Some of the images uploaded from a particular subject at a particular visit may be correctly labelled, and some incorrectly labelled.

Data that is collected from some sites may be analysed or annotated at a different site, and it can be desirable to associate the analysed or annotated results with the original images, even if they may be in different formats.

The central server 2 is therefore arranged to use prior information about the images and associated data (metadata) that is expected which typically includes any one or more of the following:

1. Details of the types of image and non-image files expected (including expected values of selected metadata values such as DICOM tags)
2. The number of visits by each subject, and the timing of the visits, for example defined in terms of time intervals between visits (in some circumstances, the total number of visits may not be defined, but the interval between them is, and the subject will repeatedly be re-imaged until a defined event happens eg: their disease starts getting worse)
3. The format of the subject identifiers and expected format of the date of birth of the subject
4. Example images of the different types, for examples images which have the same contrast and noise properties as the expected images, and also show the expected anatomy. These could be reference data from other subject or subjects, or image data collected from the subject under consideration at a previous timepoint.
5. Examples of the different non-image data types (with MIME types and expected content)
6. Information about the required labels (those required to identify the trial, the subject and those required to interpret or analyze the images and metadata), and the expected label value or values.

Some or all of this reference data is stored in a trial or clinical configuration file, which is derived from the trial protocol or clinical protocol, or histology protocol 15. For a clinical trial, the protocol is generated when the trial is planned and, the derived trial configuration file is stored on the central server 2. In healthcare applications, a protocol is defined for the treatment of patients that have similar symptoms or diagnoses or are undergoing similar treatments, and these protocols are also known in advance, though they may be more flexible than clinical trial protocols. The server 2 may obtain aspects of the trial configuration or clinical protocol by accessing a further computer system such as a Clinical Trial Management System (CTMS) or Clinical Data Management System (CDMS) or some other hospital or radiological information system. In some cases some of the data, such as example images, may be stored in a separate file or files 16.

The central server 2, specifically the matching system 11 is arranged to match in-coming imaging data comprising the image data and metadata (normally a large number of files either arriving in bulk after the trial is completed, or arriving gradually during the course of the trial) against the prior knowledge about what is expected in order to allocate correct labels to the required image attributes. The matching involves analysis of the metadata, and of the image data itself (by comparison with reference data and previously collected data). In some circumstances, the expected Subject or Patient IDs will be incorporated in the trial configuration file. When uploading files from a disk, the MIME types of the files, the names and properties of data files and the names and properties of the folders containing them can be used in the matching alongside the contents of the files themselves. When data arrives across a network, then the addresses of the computers being used and the identities of the users uploading the data can also be used in the matching process. Data is quarantined while this matching is going on, and any data for which the match confidence is below a defined threshold is left in quarantine for inspection by a user. In real time embodiments of this invention, the results of the match are presented to a user via the user interface 6 immediately following their calculation, to enable the user to appreciate whether the data uploaded matches the criterion, or to prompt for clarification or additional data.

The matching, or some aspects of it, is performed in a combined multidimensional classifier space. The dimensions correspond to different properties of the imaging data, such as values of parameters defined in the metadata or properties of the image data. For example the matching includes: matching metadata values in the incoming data against the reference metadata values. These metadata values can therefore define one or more dimensions of the classifier space. Other dimensions can relate to image derived measures such as intensity histograms. The image intensity histograms can be quite distinct for a particular type of image acquisition, and can be calculated by plotting voxel intensity (brightness) on the horizontal axis, and frequency of occurrence of this brightness on the vertical axis. Another type of image-derived measure is the degree of matching of the anatomical region or organs imaged, which can be determined by aligning the uploaded images against reference images using an image registration algorithm and ascertaining whether the overlap between the acquired and reference anatomy is sufficiently close to meet the requirements of the analysis. The reference image could be from a different subject, the same subject at an earlier time or from one or multiple atlases, or feature databases. Incoming data can therefore be matched to expected data or reference data by determining the proximity between the two in the multi-dimensional classification space. Where there are more than one set of reference or expected data, the one which is closest to the incoming data in the classification space is identified as the closest match. Once the closest match has been found a confidence parameter dependent on the proximity is associated with the match, and the incoming data can be corrected if appropriate.

A further image-derived measure is the detection and quality checking of any contrast agent used during the examination, such as oral iodinated contrast in CT or intravenous Gd-DTPA contrast in MRI. The matching of an individual image to a reference image can also be used to determine whether a contrast agent has been used correctly during the examination (both whether the contrast agent has been injected at all, and optionally also whether the timing of the injection and image collection is as prescribed). In this case, the reference image can be pre-labelled with one or more known vascular regions (e.g.: major vessels or vascular tissue), and following alignment of the current image to the reference image using an image registration algorithm, the intensity properties of the image in the region(s) of interest are compared between the current and reference image (e.g: using a comparison of the mean intensity or intensity histogram for the two images) to determine whether the pattern of intensity enhancement is consistent with the use of contrast agent in the examination, and whether the image has been acquired correctly following injection of that agent (eg: venous phase vs arterial phase). Where an image is dynamic, the change in intensity of this region with time can also be compared between the current and reference image in order to assess whether the dynamic change in contrast is consistent with correct use of the contrast agent during the examination.

As more data is passed through the system, the classifiers, which can be adaptive algorithms run on the matching system 11, can learn more about the expected study data to increase the confidence of the labelling.

Figure 3:
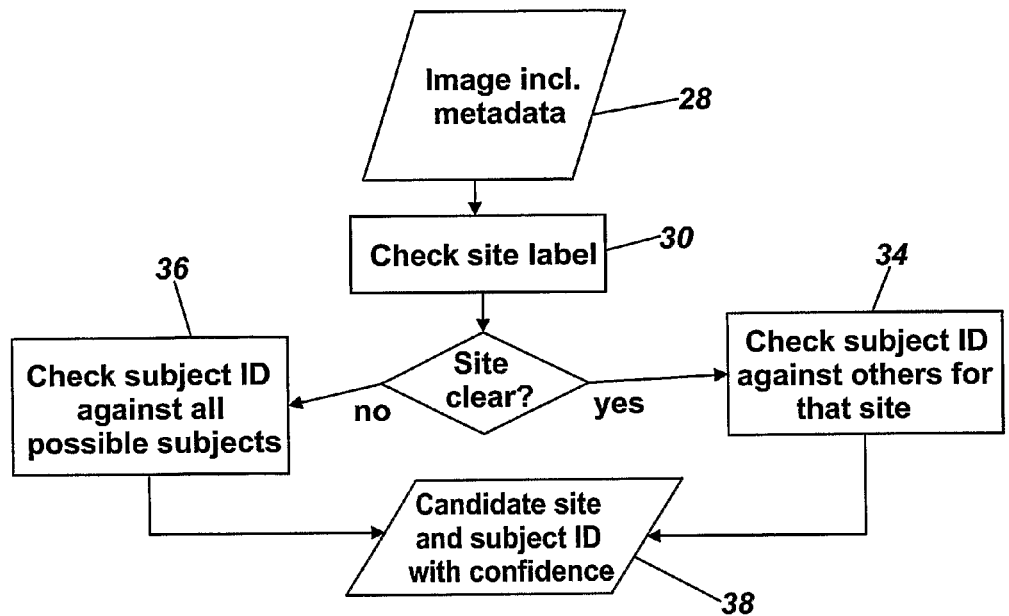
FIG. 3 is a flow diagram showing part of the operation of the system of FIG. 1.

Referring to FIG. 3 one part of the checking of incoming image data files includes checking at step 30 the site label which indicates the site at which the scan was performed. If the site label is unambiguous (e.g. it is in the correct format and corresponds to a site for which data collected at that timepoint is expected), then the process moves to step 34 where it checks the subject ID against other IDs associated with that site. If the site label is ambiguous, or if step 34 fails to produce a candidate match then the process moves to step 36 where it checks the subject ID against all possible subject IDs from all sites to identify the closest match. From the closest, or identical, subject ID the correct site with which that subject is associated can be identified. From either of steps 34 or 36 the server can generate at step 38 a candidate site and subject ID with a confidence level indicating a probability that the candidate data is correct.

Figure 4:
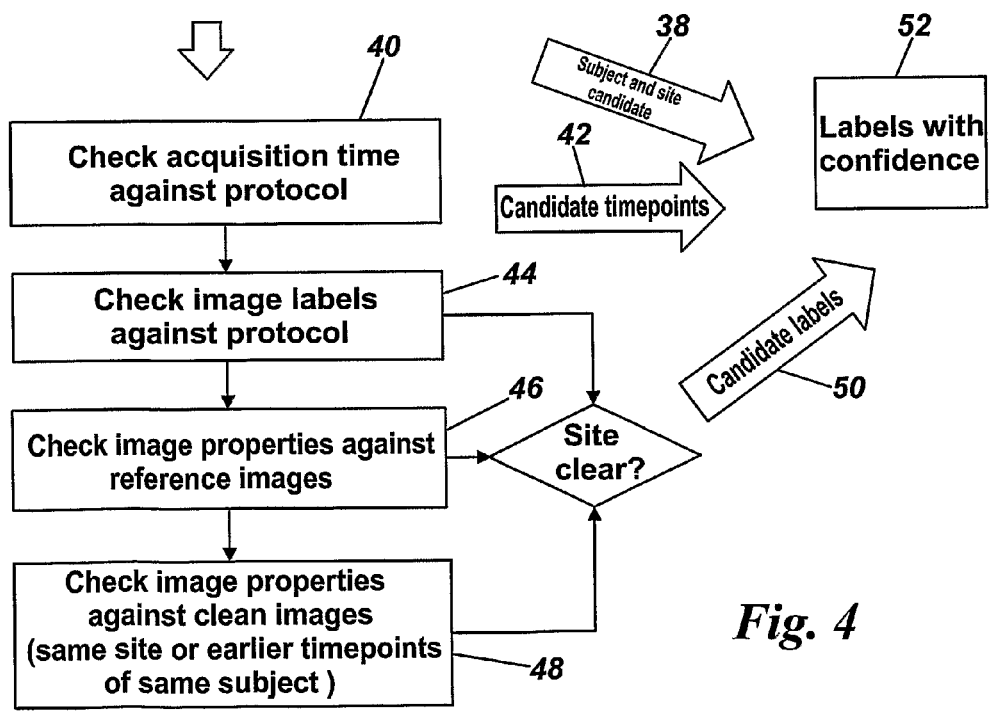
FIG. 4 is a flow diagram showing part of the operation of the system of FIG. 1.

Referring to FIG. 4, in a further part of the checking process, the acquisition times indicated in the data files (such as in the DICOM tags), for the associated images in the received data, are checked at step 40 against the expected acquisition times as defined in the trial configuration file, or as calculated from the date and time of previous data from the same subject along with between-visit intervals in the trial or clinical configuration file. This comparison identifies the most likely acquisition time point for each image, which is used as a candidate time point 42, and those candidate time points with associated confidence levels are also output. Then at step 44 the server 2 checks the labels in the images (eg: DICOM tags) and any associated data files against the labels in the trial configuration file, and identifies the most likely data labels together with a confidence level. As with the subject ID, the check can be against expected labels for the site identified in the image file, if that is matched to a valid site, and against expected labels from all sites if there is no valid site match. Then at step 46 various properties of the images in the image files are determined, by analysis of the image data, and compared with corresponding properties of the appropriate reference images 16. Properties which may be used for this comparison include the noise spectrum of the image, i.e. the level of noise as a function of spatial frequency, the signal to noise ratio of the image, image histogram metrics including skewness or similarity of match with a reference image histogram, or image features, i.e. parts of the image data corresponding to imaged parts of the subject or particular spatial patterns of noise such as may be caused by receiver or processing characteristics. At step 48 the various image properties of the received images are compared with the corresponding properties of clean images from the same site, or earlier images from scans of the same subject at earlier time points.

At each of steps 46 and 48, each of the properties which is compared has one or more labels or parameters associated with it. For example the noise spectrum of the image may be unique to a particular scanner, or a particular scanner type, and therefore a reference noise spectrum may be indicative of the image having been acquired on a particular scanner or type of scanner. Therefore the degree of similarity between the noise spectrum of the received image and those of a number of reference images may identify the scanner on which the received image was acquired, with an associated confidence determined by the degree of similarity. Reference image features may be associated with particular scan parameters, for example the part of anatomy being scanned, or the orientation of the subject during the scan. These parameters will generally be defined in the trial or clinical protocol file by means of associated metadata or labels. Therefore checking the image features against reference images can be used to identify candidate scan parameters of this nature. A further aspect of the checking relates to the metadata that describes in words the type of image collected (eg: the DICOM series description, but could be other metadata fields within the file or file or folder names). Such a description is often entered by a user and is particularly prone to error. That data is compared with other metadata to confirm that it is consistent with that, and also with properties of the image data, which depend on the type of scanner used or the type of scan performed, to check that it is consistent with that data.

In addition to the images that are typically in DICOM format, or another format that contains subject and image-specific metadata, there may be associated files that might be spreadsheets or analysed images where the identifying data is contained in the filename or directory name rather than within the file. The trial configuration file will define what type of files are expected (eg: by their MIME type or filename extension) at each time point, and the system can search a specified disk to find files of the expected type that contain relevant identifiers in the filename, directory name or within the file contents. For example, if a Microsoft excel spreadsheet is expected to go along with a particular subject, the system can search relevant portions of the computer disk from which the data is being uploaded to find any files of this type that contain the required subject ID in the file name or the directory name (matching strings using methods such as regular expressions and Levenshtein Distance). For each candidate match, a match metric is provided. If there is only one match above a pre-determined threshold, this file can be uploaded and associated with the relevant subject visit automatically. If there are multiple possible matches, then the different possible matches can be presented to the user via the user interface 6 for them to select the match that is correct.

Once the checks described above have been completed by the matching system 11, a complete candidate set of metadata, (or labels) with associated confidence levels can be defined for all image files and associated files.

Referring to FIG. 5, an example of a trial protocol defines a number of subject identities, a number of visits that each subject is expected to make to the scanner site including the identity of the site and an acceptable range of times for each of the visits, and a number of different scan images that need to be acquired at each visit, including the type of scanner and the type of image to be acquired with the scanner, and also the types of associated data that may be collected along with the images, and may also include the analysis results expected from these data. This associated data or analysis results could for example be in the form of simple tables of numbers entered by a user, or computer files generated by the scanner or by physiological monitoring devices. The acceptable range of times may be defined in absolute terms, but are more likely to be in terms of time intervals between each visit and the previous one, or each visit and a reference time point, such as a start date of the trial or initial diagnosis or commencement of a treatment protocol. These definitions of the different expected images and associated files therefore include data defining labels, characteristics and features of the expected data. In the example shown three images are required of each subject at each visit. The timing of the visits is also defined, typically in terms of an acceptable range of time intervals between each consecutive pair of visits. Referring back to FIG. 2, once the data cleaning has been performed on an individual image file, the matching system is arranged to identify a candidate image definition, i.e. a candidate location in the table of FIG. 5, for that image file. Again this can be associated with a degree of confidence or match. As the data is received, it can be displayed in a table such as that of FIG. 5 with each of the expected images or other files highlighted in a colour to indicate its current status. In this case one colour, such as green, is used to indicated clear data, another such as amber, is used to indicate ambiguous data, which needs further checking, and another colour such as red is used to indicate data that is missing.

At each stage of the checking described above, the confidence level is checked. If it is above a predetermined limit, which can be set independently for each parameter, then the image data, or the metadata, of the received imaging data file can be corrected or left as appropriate so that it corresponds to the reference data. For example, if the subject ID is very close to, but slightly different from, a valid ID, then it can be corrected automatically. If all the data in the imaging file suggest that it came from one particular scanner, apart from the scanner ID in the file metadata, then assuming the confidence is high enough the scanner ID can be corrected automatically. In other cases, where an exact match, or a match with sufficiently high confidence, cannot be found, then this can be flagged to a user for review. For example this can be done by displaying the image, and any associated metadata that is not in doubt on the display of the user interface 6, together with a list of the most likely options for the data or label that is in doubt. A user can then make the appropriate selection to correct the data by providing a suitable input at the user interface 6.

It will be appreciated that the system described has a number of advantages over previous approaches, which we illustrate using five examples.

Example 1, a trial involves 100 subjects scanned at 20 hospitals. Each subject is required to receive multiple types of imaging at each of four time points: X-ray, T1 MRI, T2 MRI, and contrast enhanced MRI. The clinical trial protocol for this trial will include a schedule of visits, which defines which sort of image should be collected from a subject at which hospital visit The data could be distributed across multiple computer systems or stored on several hundred CDs, and it is desirable to load it onto a single system, and then perform queries such as "retrieve the T1 MR scans from all subjects at time point 2" or "show all subjects for which the contrast MRI scan is missing from any time point"

Standard image archives that search on the DICOM tags, for example, cannot solve this problem, because each of the sites will have used a different Series Description in the DICOM for T1 weighted image, or contrast enhance MRI. Furthermore, the DICOM file does not contain any reference to the "time point", and just ordering the files by date does not deal with the possibility that a subject might have had an unexpected repeat scan (E.g. if they moved and were invited back a week later for another), or that a scan is missing (e.g. if the patient did not attend, or the data got lost in the post). Furthermore there is the possibility of subject or site mislabelling.

Example 2 is a research study involving functional MRI data collected from 30 subjects from 3 sites, with each subject attending for two visits. At each time point, a dynamic series of functional MRI experiments are performed while the subject is performing a task in accordance with a stimulus paradigm. In order to perform the analysis, additional image and non-image data is required, including a spreadsheet file describing the temporal stimulus, and a volumetric MRI scan. The study protocol describes the image and associated data required at each time point, and also the analysis results expected for each time point. The analysis is performed at each site individually, and the analysis of the output is additional images (in a different format to the format of the original images) and a spreadsheet. The task is to upload the original data (image and associated data), along with the results into a single system, such that all the files are grouped together and correctly labelled according to the type of scan, the type of data, the subject, the site and the visit. By correctly labelling all the data on import, the system can present users with a graphical interface that allows them to see, at a glance, which subjects have been upload completely with all results attached, and which are incomplete or do not have all results available, and to easily retrieve any images or results of interest.

Example 3, involves a large volume of legacy data from 20 different multi-site trials. Each trial has its own trial configuration file that describes the image data and associated data required for all subjects and lists all the subject IDs enrolled in that trial. The task is to upload all that legacy data onto a central system such that each image is correctly labelled with the subject ID, the site ID, the trial ID the molecule under test, and the pathology being treated. The use of the technology described in this embodiment of the invention uploads the data to enable the user to perform searches such as "find all subjects with pathology X tested with molecule Y that completed imaging from 2 or more time points", and will get back results that meet the search criteria regardless of which trial the subjects were enrolled in.

Example 4: In a clinical trial in which 1000 subjects are being imaged at 100 hospitals, it is desirable to check whether the sites have collected data that is suitable for subsequent central analysis should that analysis become necessary. The trial protocol requires that the images are correctly de-identified, and cover each subject's chest, abdomen and pelvis, that they have a slice thickness of between 2 mm and 4 mm, and that they have a contrast agent present. The system checks that the patient ID and other personally identifiable information in the image headers is in a de-identified format (and alters this automatically or through user intervention if required), checks the DICOM metadata tags to ensure that the slice thickness is in the desired range, then aligns each image with reference data (which might be data from a typical subject, or of the same subject at a previous time point) using an image registration algorithm, and uses image histogram analysis in a known vascular region to check for the presence of the contrast agents, and an image over-lap measure to determine whether the correct anatomy has been imaged. Feedback is given back to the trial organizer at each of the sites in real time as to whether the requirements of the protocol have been met.

Example 5: In a hospital all examinations of patients being treated for a particular cancer are to be reviewed for the purposes of clinical audit. Images and other clinical data from examinations of patients within the selected category are identified both using an external list of subjects and using image files and other data directly to identify all examinations that are likely to be relevant. The total uploaded data can then be ordered and searched, verified against an external list of the subjects to identify discrepancies, and then for all verified subjects checks can be made against the established protocol for treatment monitoring. The system can then provide information about errors, deviations from protocol and missed or inappropriate examinations and can provide information to link to subsequent follow-up assessment.

The embodiments of this invention described can comprehensively address the five example tasks described above by uploading this data in a way which makes it generally consistent and accurate.

The embodiments described provide a much more automated solution to data checking and cleaning compared to previous solutions, reducing the likelihood of mislabelled or wrongly-acquired data being analysed, and providing at-a-glance information about protocol compliance from all study/clinical sites. In some cases it may be possible to avoid the option of human interaction altogether, but where some cases are referred to a user for review, checking and correction as described above, the rate at which the user will have to intervene will be considerably less than in previous more manual methods and the system provides an audit trail so that the manual steps can be subsequently confirmed should the need arise.

In some cases the system can be used prospectively, in that the matching system on the server 2 is arranged to monitor the expected time of arrival of image data as defined in the trial protocol, and detect non-arrival of expected data at an expected arrival time. This can be referred to an operator to check or flagged in the report data as an error. This prompting can take place in real-time, potentially while the user is performing the upload, or even while the subject is still in the scanner.

In many cases where the imaging data is amended, a full audit trail of all data cleaning activity and other data amendments is recorded, for example in the file containing the imaging data. This allows the audit trail to be kept and checked as required.

It will be appreciated that, though the embodiments described include a central server that performs the data checking and cleaning, it is equally possible for the system to be a distributed system in which various different functions or tasks are performed on different computers, which may be remote from each other.

The embodiment focuses especially on clinical images stored in DICOM format, but images in other formats including propriety radiological imaging formats, research-data formats, image analysis formats (eg: niftii) immuno-histochemistry image formats, MR spectroscopy and other complex data types (eg physiological data from EEG, ECG or actigraphy) can be handled by some embodiments of the invention.

The invention claimed is:

1. A system for admitting medical imaging data including image data and associated metadata, the system comprising input means arranged to receive image data from at least one source, a memory having stored therein consistency data defining at least one consistency criterion wherein the consistency data includes reference data and the consistency criterion is a degree of consistency between the imaging data and the reference data, the reference data comprising at least one of reference image data and reference metadata, and processing means arranged to analyze the imaging data to determine whether it meets the consistency criterion, wherein the processing means is arranged to determine a degree of similarity between the imaging data and the reference data using a plurality of properties of the data and, if the degree of similarity is above a predetermined limit, to correct the imaging data using the reference data, the degree of similarity being measured using distance in a multi-dimensional classification space in which each dimension corresponds to a property of the data.

2. The system according to claim 1 wherein the consistency data defines at least one expected characteristic of the imaging data and the consistency criterion is that the imaging data has that expected characteristic.

3. The system according to claim 1 further comprising a user interface wherein a control means is arranged, if the degree of consistency is below a predetermined limit, to provide an indication of this via the user interface.

4. The system according to claim 3 wherein, if the degree of consistency is below a predetermined limit, the control means is arranged to display the data on the user interface for checking by a user.

5. The system according to claim 1 wherein the consistency data defines a protocol including expected imaging data sets relating to a plurality of expected images, and wherein the processing means is arranged to compare received imaging data with each of the expected imaging data sets and to identify which of them it is most consistent with.

6. The system according to claim 5 wherein each of the expected imaging data sets includes at least one of: an expected time of acquisition; an expected scanner identity; and an expected patient identity.

7. The system according to claim 1 wherein the consistency data includes reference image data and the processing means is arranged to compare image data within the received imaging data with the reference image data to determine a degree of matching between a portion of a subject's anatomy imaged in the received imaging data and a portion of anatomy imaged in the reference image data.

8. The system according to claim 7 where the processing means is arranged to compare intensity related data of the received imaging data with corresponding intensity related data of the reference image data to determine whether the relationship between the two sets of intensity related data is consistent with an expected use of contrast agent.

9. The system according to claim 8 wherein the reference image data is from a previously collected image from the same subject as the received imaging data.

10. The system according to claim 7 wherein the imaging data includes series description data and the consistency criterion relates to the consistency of the series description data with the reference image data.

11. The system according to claim 1 wherein the consistency criterion relates to consistency between different parts of the imaging data.

12. The system according to claim 11 wherein the consistency criterion relates to consistency between the image data and the metadata.

13. The system according to claim 1 wherein the consistency data includes a protocol including at least one of: subject identity, acceptable ranges of scan time points, type of imaging apparatus, and type of imaging method.

14. The system according to claim 13 wherein the protocol is a clinical trial protocol.

15. A computer implemented method of admitting data including image data and associated metadata for analysis, the method comprising defining at least one consistency criterion defined by consistency data, analyzing the image data to determine whether it meets the criterion, and if the image data does not meet the consistency criterion, amending the image data so that it does meet the consistency criterion, wherein the consistency data includes reference data and the consistency criterion is a degree of consistency between the image data and the reference data, the reference data comprising at least one of reference image data and reference metadata, wherein analyzing the image data comprises determining a degree of similarity between the image data and the reference data using a plurality of properties of the data and, if the degree of similarity is above a predetermined limit, correcting the image data using the reference data, wherein the step of determining a degree of similarity comprises measuring a distance in a multi-dimensional classification space in which each dimension corresponds to a property of the data.

* * * * *